(12) United States Patent
Schlatter et al.

(10) Patent No.: US 7,199,081 B2
(45) Date of Patent: *Apr. 3, 2007

(54) AQUEOUS COMPOSITIONS FOR SEED TREATMENT

(75) Inventors: Christian Schlatter, Greensboro, NC (US); Ravi Ramachandran, Guelph (CA)

(73) Assignee: Syngenta Crop Protection, Inc., Greensboro, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/069,021

(22) Filed: Feb. 28, 2005

(65) Prior Publication Data

US 2005/0209103 A1 Sep. 22, 2005

Related U.S. Application Data

(63) Continuation of application No. 10/256,297, filed on Sep. 27, 2002, now Pat. No. 6,884,754.

(60) Provisional application No. 60/325,829, filed on Sep. 28, 2001.

(51) Int. Cl.
*A01N 25/30* (2006.01)
*A01N 43/30* (2006.01)
*A01N 43/54* (2006.01)
*A01N 43/653* (2006.01)
*A01P 3/00* (2006.01)

(52) U.S. Cl. ............... 504/100; 514/383; 514/417; 514/421; 514/429; 514/433; 514/476; 514/517; 514/538; 514/975

(58) Field of Classification Search ............... 504/100; 514/383, 417, 421, 427, 429, 433, 476, 517, 514/538, 975
See application file for complete search history.

(56) References Cited

U.S. PATENT DOCUMENTS

| | | | |
|---|---|---|---|
| 4,161,397 | A | 7/1979 | Bellet et al. |
| 4,306,027 | A | 12/1981 | Alexander et al. |
| 4,755,468 | A | 7/1988 | Jung et al. |
| 5,599,583 | A | 2/1997 | Lew et al. |
| 5,684,025 | A | 11/1997 | Tsao et al. |
| 5,846,905 | A | 12/1998 | Frisch et al. |
| 6,503,904 | B2 | 1/2003 | Schneidersmann |
| 6,746,988 | B2 * | 6/2004 | Hopkinson et al. ......... 504/127 |
| 6,884,754 | B1 | 4/2005 | Schlatter et al. |

FOREIGN PATENT DOCUMENTS

| | | |
|---|---|---|
| EP | 0609099 | 8/1994 |
| EP | 0790000 | 8/1997 |
| EP | 1319336 | 6/2003 |
| WO | 9500019 | 1/1995 |
| WO | 9940784 | 8/1999 |
| WO | 0028825 | 5/2000 |
| WO | 0160159 | 8/2001 |

OTHER PUBLICATIONS

Doyle P et al: "New Generation Seed Treatment Products for Canola (*Brassica Napus, B. Campestris*) and Mustard (*Sinapis Alba, Brassica Juncea*)", British Crop Protection Council Monograph, British Crop Protection Council, London, GB, No. 76, 2001, pp. 173-180, XP009015867, ISSN: 0306-3941, abstract.

Jonitz A et al: "Seed Testing and the Effect of Insecticidal Active Ingredients on the Germination and Emergence of Hybrid Maize Seed", Pflanzenschutz Nachrichten Bayer, Bayer, Leverkussen, DE, vol. 56, No. 1, 2003, pp. 173-207, XP009057321, ISSN: 0340-1723, pp. 188, col. 1, paragraph 2 figures.

"Agrochemical-coated rought rice deeds for pest resistance-prepd by coating seeds with adhesive resin fluid contg pesticide and surfacant", DERWENT, 1996, XP002286597, abstract.

Maude, S J: "The effects of surfactant and water volume on the coverage of seed surface by a seed treatment formulation"; Brighton Crop Protection Conference Pests and Idseases, vol. 2, 2002, pp. 507-514, XP009034608, ISSN: 0955-1506, abstract.

* cited by examiner

*Primary Examiner*—S. Mark Clardy
(74) *Attorney, Agent, or Firm*—Jacqueline Haley

(57) ABSTRACT

An aqueous composition suitable for applying fungicides to plant propagation materials is provided, comprising water and a blend of the following components, by weight:
a) 2–10% of a surface-active agent comprising a1) at least one anionic surfactant;
b) 0.5–10% of at least one polymer selected from water-dispersible polymers and water-soluble film-forming polymers;
c) 4–20% of at least one inorganic solid carrier; and
d) 3–20% of at least one antifreeze agent.

In one embodiment, the composition comprises a fungicidally effective amount of at least one fungicidally active compound.

The inventive composition is storage stable, ready-to-apply (RTA), ecologically and toxicologically favorable and has good fungicidal efficacy.

12 Claims, No Drawings

AQUEOUS COMPOSITIONS FOR SEED TREATMENT

This application is a continuation of U.S. application Ser. No. 10/256,297, filed on Sep. 27, 2002, now U.S. Pat. No. 6,884,754, which claims priority to U.S. provisional application Ser. No. 60.325,829, filed on Sep. 28, 2001, now abandoned.

TECHNICAL FIELD

The present invention relates to aqueous compositions, to the preparation of such compositions and to a method of using such compositions to combat phytopathogenic fungi. The aqueous compositions of the invention have particular application in the protection of plant propagation materials, such as seeds, against fungal disease.

BACKGROUND

The use of synthetic fungicides to control phytopathogenic fungi in crops is a wide spread practice. This practice has gained a high degree of commercial success because it has been shown that such control can increase crop yield. Fungicides can be applied directly to plant propagation materials (such as seeds) prior to sowing and/or are used in foliar or furrow applications.

Seed treatments are used on a large variety of crops to control a large variety of pests. Seed treatments are commonly used to ensure uniform stand establishment by protecting against soilborne diseases and insects. Systemic seed treatments may provide an alternative to traditional broadcast sprays of foliar fungicides or insecticides for certain early season airborne diseases and insects.

In general, fungicidal seed treatments are used for three reasons: (1) to control soil-borne fungal disease organisms (pathogens) that cause seed rots, damping-off, seedling blights and root rot; (2) to control fungal pathogens that are surface-borne on the seed, such as those that cause covered smuts of barley and oats, bunt of wheat, black point of cereal grains, and seed-borne safflower rust; and (3) to control internally seed-borne fungal pathogens such as the loose smut fungi of cereals.

Fungicide seed treatments come in a variety of formulations: dry flowables (DF), liquid flowables (LF), true liquids (TL), emulsifiable concentrates (EC), dusts (D), wettable powders (WP), suspoemulsions (SE), water-dispersible granules (WG) and others. Some are registered for use only by commercial applicators using closed application systems, others are readily available for on-farm use as dusts, slurries, water soluble bags, or liquid ready-to-apply formulations.

Commercial seed treatment is often desirable due to the specialized equipment required to properly apply treatments or to treat large volumes of seed. An important concern of the commercial treater is equipment performance to ensure the delivery of a proper amount of active ingredient to the seed. This has become especially important with more modern fungicides that require only very small amounts of material (down to 1 g active ingredient per hundred weight of seed).

Conveniently, many seed treatment materials also are available for on-farm use. These are known as hopper-box or planter-box treatments wherein liquid or dry formulations are applied to seed as it passes through an auger from the transport bin or truck to the planter boxes. These formulations are a very convenient way to apply seed treatment onto bulk seed right before planting. Conventional dry treatments generally are formulated with talc or graphite which adheres the treatment chemical to the seed. Conventional liquid hopper-box treatments generally are made available as a fast-drying formulations. In any case, good seed coverage is required for maximum benefit from any seed treatment formulation.

However, obtaining thorough seed coverage can be difficult when attempting to treat seed. For example, dry formulations can present unacceptable worker exposure to the fungicidal active ingredient. Certain liquid formulations can become inhomogeneous on storage, such that particle size or viscosity do not remain constant. Additional problems can arise such as unacceptable drying times, material build-up in the seed treater, low seed flowability, poor seed coverage and dust-off of the fungicide from the seed prior to planting. As a result, handling is rendered difficult and the biological efficacy of the seed treatment is reduced.

There is a need in the art for alternative new liquid fungicidal seed treatment compositions that are effective for use with both commercial and on-farm seed treatment equipment.

SUMMARY

It has now been found, surprisingly, that specific filled aqueous compositions based on the combination of a surfactant, a water-soluble or water-dispersible film-forming polymer, an inorganic carrier and an antifreeze agent are storage stable, have improved flowability and have good adherence to plant propagation material with low dust-off, and have excellent performance on cold or frozen seed. The aqueous compositions of the invention have particular application in the protection of plant propagation materials, such as seeds, against fungal disease when combined with one or more fungicides.

The present invention thus provides an aqueous composition suitable for applying fungicides to plant propagation materials comprising water and a blend of the following components, by weight:
a) 2–10% of a surface-active agent comprising a1) at least one anionic surfactant;
b) 0.5–10% of at least one water-dispersible or water-soluble film-forming polymer;
c) 4–20% of at least one inorganic solid carrier; and
d) 3–25% of at least one antifreeze agent.

In one embodiment, the aqueous composition comprises a fungicidally effective amount of at least one fungicidally active compound.

The aqueous compositions are prepared by intimately mixing the components with water, optionally using a concentrated premix prepared by wet milling the solid components, until an evenly dispersed phase is achieved.

The invention also provides for plant propagation materials treated with the aqueous composition and for a method for reducing fungal infestation of plant propagation materials such as seeds. The method comprises contacting the seeds with an aqueous fungicidal composition according to the invention described above.

DETAILED DESCRIPTION

The inventors have discovered that a specific combination of surfactants (a), film-forming polymers (b), carriers (c) and antifreeze agents (d) when used together provide aqueous compositions that are storage stable and are suitable for use in normal seed treatment equipment, such as a slurry seed treater, direct treater, panogen treater or a mist-o-matic treater as well as on-farm hopper-box or planter-box treatments. Propagation materials treated with the aqueous compositions dry quickly, have good flowability, suitable coverage and have little or no dust-off. The aqueous compositions are advantageously combined with a fungicidally effective amount of at least one fungicide.

The term "fungicide" as utilized herein is intended to cover compounds active against phytopathogenic fungi that may belong to a very wide range of compound classes. Examples of compound classes to which the suitable fungicidally active compound may belong include both room temperature (25° C.) solid and room temperature liquid fungicides such as: triazole derivatives, strobilurins, carbamates (including thio- and dithiocarbamates), benzimidazoles (thiabendazole), N-trihalomethylthio compounds (captan), substituted benzenes, carboxamides, phenylamides and phenylpyrroles, and mixtures thereof.

Examples of suitable individual compounds of the above mentioned compound classes are listed below. Where known, the common name is used to designate the individual compounds (q.v. the Pesticide Manual, 12th edition, 2001, British Crop Protection Council).

Suitable triazole derivatives include propiconazole, difenconazole, tebuconazole, tetraconazole and triticonazole.

Suitable strobilurins include trifloxystrobin, azoxystrobin, kresoxim-methyl and picoxystrobin.

Suitable carbamates include thiram.

Suitable substituted benzenes include PCNB and chlorothalonil.

Suitable carboxamides include carboxin.

Specific phenylamides usable in the compositions and methods falling within the scope of the present invention include metalaxyl; metalaxyl consisting of more than 70% by weight of the R-enantiomer; metalaxyl consisting of more than 85% by weight of the R-enantiomer; metalaxyl consisting of more than 92% by weight of the R-enantiomer; metalaxyl consisting of more than 97% by weight of the R-enantiomer; and mefenoxam (i.e., R-metalaxyl or metalaxyl-M).

A specific phenylpyrrole usable in the compositions and methods falling within the scope of the present invention is fludioxonil.

Other suitable fungicidal compounds that may mentioned are Benomyl (also known as Benlate), Bitertanol, Carbendazim, Capropamid, Cymoxanil, Cyprodinil, Ethirimol, Fenpiclonil, Fenpropimorph, Fluquinconazole, Flutolanil, Flutriafol, Fosetyl-aluminum, Fuberidazole, Guazatine, Hymexanol, Kasugamycin, Imazalil, Imibenconazole, Iminoctadine-triacetate, Ipconazole, Iprodione, Mancozeb, Maneb, Mepronil, Metalaxyl, Metalaxyl-M (Mefenoxam), Metconazole, Metiram, MON 65500 (Silthiopham-ISO proposed), Myclobutanil, Nuarimol, Oxadixyl, Oxine-copper, Oxolinic acid, Pefurazoate, Pencycuron, Prochloraz, Propamocarb hydrochloride, Pyroquilon, Silthiopham—see MON 65500, Tecnazene, Thifluzamide, Thiophenate-methyl, Tolclofos-methyl, Triadimenol, Triazoxide and Triflumizole.

The fungicidally active compounds are employed in a fungicidally effective amount in the composition.

Mixtures of one or more of the foregoing fungicidally active compounds also are usable as an active component in the practice of the present invention.

In one embodiment, mixtures of at least one ambient liquid fungicide (for example, a phenylamide such as R-metalaxyl) and at least one ambient solid fungicide (for example, a phenylpyrrole such as fludioxonil) are employed.

In one embodiment, the fungicidally active compound or compound mixture is present in the composition in an amount of from about 0.5% to about 50% by weight, more specifically, from 2 to about 20% by weight of the entire composition.

Surface Active Agent

The aqueous compositions contain at least about 2% up to about 10% by weight of a surface-active agent (a). In one embodiment, the aqueous compositions contain from 3% up to 7% by weight of a surface-active agent (a).

The surface active agent (a) comprises (a1) at least one anionic surfactant. In general, the anionic surfactant may be any known in the art. Suitable anionic surfactants are in general oligomers and polymers, as well as polycondensates, which contain a sufficient number of anionic groups to ensure their water-solubility. Suitable anionic surfactants include alcohol sulfates, alcohol ether sulfates, alkylaryl ether sulfates, alkylaryl sulfonates such as alkylbenzene sulfonates and alkylnaphthalene sulfonates and salts thereof, alkyl sulfonates, mono- or di-phosphate esters of polyalkoxylated alkyl alcohols or alkylphenols, mono- or di-sulfosuccinate esters of $C_{12}$–$C_{15}$ alkanols or polyalkoxylated $C_{12}$–$C_{15}$ alkanols, alcohol ether carboxylates, phenolic ether carboxylates, polybasic acid esters of ethoxylated polyoxyalkylene glycols consisting of oxybutylene or the residue of tetrahydrofuran, sulfoalkylamides and salts thereof such as N-methyl-N-oleoyltaurate Na salt, polyoxyalkylene alkylphenol carboxylates, polyoxyalkylene alcohol carboxylates alkyl polyglycoside/alkenyl succinic anhydride condensation products, alkyl ester sulfates, napthalene sulfonates, naphthalene formaldehyde condensates, alkyl sulfonamides, sulfonated aliphatic polyesters, sulfate esters of styrylphenyl alkoxylates, and sulfonate esters of styrylphenyl alkoxylates and their corresponding sodium, potassium, calcium, magnesium, zinc, ammonium, alkylammonium, diethanolammonium, or triethanolammonium salts, salts of ligninsulfonic acid such as the sodium, potassium, magnesium, calcium or ammonium salt, polyarylphenol polyalkoxyether sulfates and polyarylphenol polyalkoxyether phosphates, and sulfated alkyl phenol ethoxylates and phosphated alkyl phenol ethoxylates.

Specific examples of suitable anionic surfactants include: Geropon T77 (Rhodia) (N-methyl-N-oleoyltaurate Na salt); Soprophor 4D384 (Rhodia) (tristyrylphenol sulphate); Reax 825 (Westvaco) (ethoxylated lignin sulfonate); Stepfac 8171 (Stepan) (ethoxylated nonylphenol phosphate ester); Ninate 401-A (Stepan) (calcium alkylbenzene sulfonate); Emphos CS-131 (Witco) (ethoxylated nonylphenol phosphate ester); and Atphos 3226 (Uniqema) (ethoxylated tridecylalcohol phosphate ester). Suitable anionic surfactants can be prepared by methods known per se and also are commercially available.

The surface-active agent comprising a1) at least one anionic surfactant may optionally further comprise a2) one or more nonionic surfactants. As used herein, "nonionic surfactants" are different compounds from the water-dispersible and water-soluble polymers b) described herein.

Exemplary nonionic surfactants include polyarylphenol polyethoxy ethers, polyalkylphenol polyethoxy ethers, polyglycol ether derivatives of saturated fatty acids, polyglycol ether derivatives of unsaturated fatty acids, polyglycol ether derivatives of aliphatic alcohols, polyglycol ether derivatives of cycloaliphatic alcohols, fatty acid esters of polyoxyethylene sorbitan, alkoxylated vegetable oils, alkoxylated acetylenic diols, polyalkoxylated alkylphenols, fatty acid alkoxylates, sorbitan alkoxylates, sorbitol esters, $C_8$–$C_{22}$ alkyl or alkenyl polyglycosides, polyalkoxy styrylaryl ethers, alkylamine oxides, block copolymer ethers, polyalkoxylated fatty glyceride, polyalkylene glycol ethers, linear aliphatic or aromatic polyesters, organo silicones, polyaryl phenols, sorbitol ester alkoxylates, and mono- and diesters of ethylene glycol and mixtures thereof.

Specific examples of suitable nonionic sufactants include: Genapol X-060 (Clariant) (ethoxylated fatty alcohol); Sorpohor BSU (Rhodia) ethoxylated tristyrylphenol; Makon TD-6 (Stepan) (ethoxylated fatty alcohol); BRIJ 30 (Uniqema) (ethoxylated lauryl alcohol); Witconol CO-360 (Witco) (ethoxylated castor oil); and Witconol NP-60 (Witco) (ethoxylated nonylphenol). Suitable nonionic surfactants can be prepared by methods known per se and also are commercially available.

In addition to anionic and nonionic surfactants, certain cationic or zwitterionic surfactants a3) also are suitable for use in the present invention such as alkanol amides of $C_8$–$C_{18}$ fatty acids and $C_8$–$C_{18}$ fatty amine polyalkoxylates, $C_{10}$–$C_{18}$ alkyldimethylbenzylammonium chlorides, coconut alkyldimethylaminoacetic acids, and phosphate esters of $C_{8-18}$ fatty amine polyalkoxylates.

In one embodiment, a mixture of surfactants (a1), (a2) and optionally (a3) is employed as follows:

(1) 0.5–4% by weight of a wetting agent selected from (a1) at least one anionic surfactant. Suitable anionic surfactant wetting agents include sulfoalkylamides and salts thereof such as N-methyl-N-oleoyltaurate Na salt, alkylaryl sulfonates such as alkylbenzene sulfonates and alkylnaphthalene sulfonates and salts thereof and salts of ligninsulfonic acid;

(2) 1–4% by weight of a dispersing agent selected from (a1) at least one anionic surfactant. Suitable anionic surfactant dispersing agents include sulfate esters of styrylphenyl alkoxylates, and sulfonate esters of styrylphenyl alkoxylates and their corresponding sodium, potassium, calcium, magnesium, zinc, ammonium, alkylammonium, diethanolammonium, or triethanolammonium salts;

(3) 1 to 5% by weight of an emulsifying agent selected from (a1) at least one anionic surfactant, (a2) at least one nonionic surfactant and a mixture thereof. Suitable anionic/nonionic surfactant emulsifiers include salts of ethoxylated alkylphenols, polyoxyethylene-polyoxypropylene alkylphenols, (fatty) alcohol ethoxylates and ethoxylated tristyrylphenols.

Film-Forming Polymer

The aqueous composition also includes (b) at least one polymer selected from water-soluble and water-dispersible film-forming polymers. Suitable polymers have an average molecular weight of at least about 1,000 up to about 100,000; more specifically at least about 5,000, up to about 100,000. The aqueous compositions generally contain from about 0.5% to about 10% by weight of the composition of polymer (b). In a specific embodiment, the compositions contain from about 1.0% up to about 5% by weight of a film-forming polymer (b).

Suitable polymers are selected from b1) alkyleneoxide random and block copolymers such as ethylene oxide-propylene oxide block copolymers (EO/PO block copolymers) including both EO-PO-EO and PO-EO-PO block copolymers;

ethylene oxide-butylene oxide random and block copolymers, $C_{2-6}$ alkyl adducts of ethylene oxide-propylene oxide random and block copolymers, $C_{2-6}$ alkyl adducts of ethylene oxide-butylene oxide random and block copolymers, b2) polyoxyethylene-polyoxypropylene monoalkylethers such as methyl ether, ethyl ether, propyl ether, butyl ether or mixtures thereof.

b3) vinylacetate/vinylpyrrolidone copolymers, b4) alkylated vinylpyrrolidone copolymers, b5) polyvinylpyrrolidone, and b6) polyalkyleneglycol including the polypropylene glycols and polyethylene glycols.

Specific examples of suitable polymers include Pluronic P103 (BASF) (EO-PO-EO block copolymer), Pluronic P65 (BASF) (EO-PO-EO block copolymer), Pluronic P108 (BASF) (EO-PO-EO block copolymer), Vinamul 18160 (National Starch) (polyvinylacetate), Agrimer 30 (ISP) (polyvinylpyrrolidone), Agrimer VA7w (ISP) (vinyl acetate/vinylpyrrolidone copolymer), Agrimer AL 10 (ISP) (alkylated vinylpyrrolidone copolymer), PEG 400 (Uniqema) (polyethylene glycol), Pluronic R 25R2 (BASF) (PO-EO-PO block copolymer), Pluronic R 31R1 (BASF) (PO-EO-PO block copolymer) and Witconol NS 500LQ (Witco) (butanol PO-EO copolymer).

Carrier

The aqueous composition also comprises (c), at least about 4 and up to about 20%, more specifically from 5 to about 15% of at least one inorganic solid carrier.

The inorganic solid carrier is a natural or synthetic solid material that is insoluble in water. This carrier is generally inert and acceptable in agriculture, especially on the treated seed or other propagation material. It can be chosen, for example, from clay, diatomaceous earth, natural or synthetic silicates, titanium dioxide, magnesium silicate, aluminum silicate, talc, pyrophyllite clay, silica, attapulgite clay, kieselguhr, chalk, lime, calcium carbonate, bentonite clay, Fuller's earth, and the like such as described in the CFR 180.1001. (c) & (d).

Antifreeze

The aqueous composition also comprises (d), at least about 3 and up to about 25% of at least one antifreeze agent, more specifically from 6 to about 20% by weight.

Specific examples of suitable antifreezes include ethylene glycol, 1,2-propylene glycol, 1,3-propylene glycol, 1,2-butanediol, 1,3-butanediol, 1,4-butanediol, 1,4-pentanediol, 3-methyl-1,5-pentanediol, 2,3-dimethyl-2,3-butanediol, trimethylol propane, mannitol, sorbitol, glycerol, pentaerythritol, 1,4-cyclohexanedimethanol, xylenol, bisphenols such as bisphenol A or the like. In addition, ether alcohols such as diethylene glycol, triethylene glycol, tetraethylene glycol, polyoxyethylene or polyoxypropylene glycols of molecular weight up to about 4000, diethylene glycol monomethylether, diethylene glycol monoethylether, triethylene glycol monomethylether, butoxyethanol, butylene glycol monobutylether, dipentaerythritol, tripentaerythritol, tetrapentaerythritol, diglycerol, triglycerol, tetraglycerol, pentaglycerol, hexaglycerol, heptaglycerol, octaglycerol and the like.

As a particular subset of suitable antifreeze materials there can be mentioned ethylene glycol, propylene glycol and glycerin.

Additional Components

The composition optionally contains (e) at least one thickener.

In one embodiment, the thickener is present in the aqueous composition in an amount from about 0.01% to about 25% w/w, more specifically from 0.02 to 10% by weight of the entire composition.

Illustrative of thickeners (water-soluble polymers which exhibit pseudoplastic properties in an aqueous medium) are gum arabic, gum karaya, gum tragacanth, guar gum, locust bean gum, xanthan gum, carrageenan, alginate salt, casein, dextran, pectin, agar, 2-hydroxyethyl starch, 2-aminoethyl starch, 2-hydroxyethyl cellulose, methyl cellulose, carboxymethyl cellulose salt, cellulose sulfate salt, polyacrylamide, alkali metal salts of the maleic anhydride copolymers, alkali metal salts of poly(meth)acrylate, and the like.

As suitable thickeners there may also be mentioned attapulgite-type clay, carrageenan, croscarmellose sodium, furcelleran, glycerol, hydroxypropyl methylcellulose, polystyrene, vinylpyrrolidone/styrene block copolymer, hydroxypropyl cellulose, hydroxypropyl guar gum, and sodium carboxymethylcellulose. Xanthan gum is preferred.

The aqueous composition according to the invention can be employed together with the adjuvants customary in formulation technology, biocides, biostats, emulsifiers (lethicin, sorbitan, and the like), antifoam agents or application-promoting adjuvants customarily employed in the art of formulation. In addition, there may be mentioned inoculants and brighteners.

Additionally, a coloring agent, such as a dye or pigment (and the like such as described in the CFR 180.1001) is included in the seed coating so that an observer can immediately determine that the seeds are treated. The dye is also useful to indicate to the user the degree of uniformity of the coating applied.

The inventive compositions contain and/or may be applied together or sequentially with further active compounds. These further compounds can be fertilizers or micronutrient donors or other preparations that influence plant growth. They can also be selective herbicides, insecticides, fungicides, bactericides, insect growth regulators, plant growth regulators, nematicides, molluscicides or mixtures of several of these preparations.

Process

The aqueous fungicidal compositions of the invention can be prepared by processes known in the art.

In one embodiment, the aqueous fungicidal compositions of the invention can be prepared by a process which comprises the steps: (a) forming a premix with at least one solid fungicidally active compound and at least one surfactant; (b) forming a premix of a carrier and water, and (c) sequentially adding the premixes (a) and (b) and the remaining ingredients to water while stirring to form a homogeneous composition.

In one aspect, the solid fungicidally active compounds may be wet milled prior to being added to the mixture (c).

The final composition can be screened if desired to remove any insoluble particles.

Aqueous Composition

Fungicidal compositions in accordance with the invention may take the form of aqueous solutions, dispersions, suspensions, emulsions or suspoemulsions. In one embodiment, the composition is a ready for use suspension or suspoemulsion.

The average size of the suspended particles is 0.1 to 20, specifically 1.5 to 5 microns when measured with a laser particle analyzer, e.g a CILAS 920 apparatus.

The viscosity of the aqueous composition is 50 to 2000, more specifically 100 to 1000 mPas when measured with a BROOKFIELD viscometer with spindle 3 at 30 rpm and 25° C.

The aqueous compositions according to the invention are stable and maintain their viscosity and homogeneity for at least 12 months at 25° C.

Use

For the purposes of this invention, seed treatments are defined as chemical or biological substances that are applied to seeds or vegetative plant propagation materials to control disease organisms, insects, or other pests. The seed treatment composition of the invention includes fungicides, but can also include other pesticides such as bactericides and insecticides. Most seed treatments are applied to true seeds, which have a seed coat surrounding an embryo. However, some seed treatments can be applied to vegetative plant propagation materials such as rhizomes, bulbs, corms or tubers.

In general, the amount of fungicide, insecticide or other ingredients used in the seed treatment are employed in amounts that do not inhibit generation of the seed or cause phytotoxic damage to the seed. The total amount of active ingredients is generally in the range of from about 0.5% to about 50% by weight, more specifically, from 2 to about 20% by weight of the entire composition.

The aqueous fungicidal compositions of the invention are formulated for protecting cultivated plants and their propagation materials. The inventive compositions are advantageously formulated for seed treatment applications against diseases in the soil, which mostly occur in the early stages of plant development. For example, the compositions can be formulated to target pathogens including *Pythium, Tilletia, Gerlachia, Septoria, Ustilago, Fusarium, Rhizoctonia* (so-called "damping off complex"); Oomycetes such as *Phytophthora, Plasmopara, Pseudoperonospora, Bremia* etc. as well as against the *Botrytis* species, *Pyrenophora, Monilinia* and further representatives of the Ascomycetes, Deuteromycetes and Basidiomycetes classes.

Suitable target crops are especially potatoes, cereals, (wheat, barley, rye, oats, rice), maize, sugar beet, cotton, millet varieties such as sorghum, sun flowers, beans, peas, oil plants such as canola, rape, soybeans, cabbages, tomatoes, eggplants (aubergines), pepper and other vegetables and spices as well as ornamental shrubs and flowers.

Suitable target crops also include transgenic crop plants of the foregoing varieties. The transgenic crop plants used according to the invention are plants, or propagation material thereof, which are transformed by means of recombinant DNA technology in such a way that they are—for instance—capable of synthesizing selectively acting toxins as are known, for example, from toxin-producing invertebrates, especially of the phylum Arthropoda, as can be obtained from *Bacillus thuringiensis* strains; or as are known from plants, such as lectins; or in the alternative capable of expressing a herbicidal or fungicidal resistance. Examples of such toxins, or transgenic plants which are capable of synthesizing such toxins, have been disclosed, for example, in EP-A-0 374 753, WO 93/07278, WO 95/34656, EP-A-0 427 529 and EP-A-451 878 and are incorporated by reference in the present application.

The inventive compositions are particularly suited for dressing applications on plant propagation material. The latter term embraces seeds of all kinds (fruit, tubers, grains), cuttings, cut shoots and the like. The preferred field of application is the treatment of all kinds of seeds (as specified in the target crops above), and in particular the seed treatment of canola, maize, cereals, soybeans and other legumes and crops that are susceptible.

The techniques of seed treatment application are well known to those skilled in the art, and they may be used readily in the context of the present invention. The aqueous fungicidal composition of the invention is applied to the seed as slurry or a soak. There also may be mentioned, e.g., film coating or encapsulation. The coating processes are well known in the art, and employ, for seeds, the techniques of film coating or encapsulation, or for the other multiplication products, the techniques of immersion. Needless to say, the method of application of the inventive compositions to the seed may be varied and the invention is intended to include any technique that is to be used.

One method of applying the aqueous fungicidal composition according to the invention consists in spraying or wetting the plant propagation material with the aqueous liquid preparation, or mixing the plant material with such liquid preparation. Also, before the application, the composition of the invention may be diluted with water by simple mixing at ambient temperature in order to prepare an on-farm seed treatment formulation.

In one embodiment a concentrate or dilute composition of the invention is applied to seed by spraying, wetting or mixing in a volume of from 200 ml to 3 liters of aqueous composition per 100 kg of seed, more specifically, from 400 ml to 2 liters of aqueous composition per 100 kg of seed.

As noted above, the compositions of this invention may be formulated or mixed in the seed treater tank or combined on the seed by overcoating with other seed treating agents. The agents to be mixed with the compounds of this invention may be for the control of pests, nutrition, and the control of plant diseases.

The inventive aqueous fungicidal composition has particular application to concurrent (such as by slurry) and sequential seed treatments.

The aqueous compositions of the invention are both cold and heat stable and can be applied to seeds at temperatures ranging from −20 to 40° C.

Seeds treated with the aqueous composition of the invention have a drying time ranging from 20 to 60 seconds when being treated at room temperature.

The aqueous compositions of the invention typically are distributed in a storage and shipping system comprising a container ranging in capacity from about 0.1 liter to about 2000 liters.

For example, the aqueous compositions of the invention can be distributed in small containers, ranging in capacity from about 0.1 liter to about 10 liters, including the standard 2.5 gallon (9.46 liter) containers widely used in the United States, which typically take the form of jugs or flasks with a replaceable screw-cap. They are generally designed for single use and are typically not returned to the supplier when empty, instead being disposed of by the end user in accordance with local agricultural chemical container disposal guidelines, procedures, regulations or laws. Commonly, a plurality of these small containers are packaged within a single box and a plurality of such boxes are shipped on a pallet. During shipment, the small containers (usually within boxes on pallets) can be disposed in an enclosed volume such as provided by a rail boxcar or road truck, the hold of a ship or aircraft, or a modular box container adapted for transport by road, rail and water.

Larger single-use containers, ranging in capacity up to about 200 liters, for example about 50 to about 200 liters, are commonly in the form of drums, and can be shipped in an enclosed volume as described above, one or more per pallet or unpalleted.

The aqueous compositions of the invention also can be distributed in a large refillable container sometimes known as a bulk or minibulk tank, which typically has an integral pump or connector for an external pump to permit transfer of liquid. Bulk or minibulk tanks having a capacity of about 200 to about 2000 liters or more are typically returned to the supplier when empty and are commonly shipped on a pallet.

The smaller containers typically are constructed of a durable plastic such as high density polyethylene (HDPE), although large bulk tanks are often constructed of other materials such as stainless steel.

A principal feature of the inventive composition is that it provides a treated seed with increased adherence which results in decreased dustiness and the subsequent elimination of related dust problems. Elimination of the dust associated with many seed treatments also eliminates the associated health hazards to those who work with treated seeds, such as processing plant employees, truck drivers, warehouse workers, and farmers.

Still another advantage of this invention is the uniform coating of-seeds with non-dusting seed treatment which will not interfere with germination and sprouting of the seed but which will protect the seed against seed-borne pathogens.

EXAMPLES

In order that those skilled in the art will be better able to practice the invention, the following examples are given by way of illustration and not by way of limitation. In the following examples, as well as elsewhere in the specification and claims, temperatures are in degrees Celsius, the pressure is atmospheric and all parts are by weight, unless otherwise clearly indicated.

The registered trademarks and other designations denote the following products:

| Product | Composition | Source |
|---|---|---|
| Surfactants | | |
| Geropon T77 | methyl oleytaurate Na-salt | Rhodia |
| Soprophor 4D384 | ethoxylated Tristyrylphenol sulphates | Rhodia |
| Stepan Agent 1411-80A | 4EO nonylphenol/6EO Tallow amine | Stepan |
| Reax 825 | ethoxylated lignin sulfonate | Westvaco |
| Genapol X-060 | Ethoxylated fatty alcohol | Clariant |
| Polymers | | |
| Agrimer ST | Vinylpyrrolidone/styrene block copolymer | ISP |
| Pluronic P103 | EO-PO-EO block copolymer | BASF |
| Pluronic P65 | EO-PO-EO block copolymer | BASF |
| Pluronic P108 | EO-PO-EO block copolymer | BASF |
| Vinamul 18160 | Polyvinylacetate | National Starch |
| Agrimer 30 | Polyvinylpyrrolidone | ISP |
| Agrimer VA 7w | Vinylacetate/vinylpyrrolidone copolymer | ISP |
| Agrimer AL 10 | Alkylated polyvinylpyrrolidone | ISP |
| PEG 400 | Polyethyleneglycol | Unichema |
| Witconol NS 500LQ | Butanol PO-EO block copolymer | Witco |
| Carriers | | |
| Volcaly 325mesh | Aluminum silicate | American Coloid |
| Auxilaries | | |
| Irgalite Red C2B | Pigment red C2B | Ciba Speciality |
| Antifoam A | Silicon oil | Dow Corning |
| Proxel GXL | Bactericide (1,2-Benzisothiazol-3(2H)-one) | |
| Rhodopol 23 | Xanthan gum | |

Example 1

Preparation of an Aqueous Seed Treatment Formulation 1.1—10% Solid Carrier Gel

Aluminium silicate (Volclay) is added to water with good agitation in sufficient amounts to prepare a 10%-gel. Mixing is continued until the Volclay is completely dispersed.

1.2—2%—Aqueous Thickener Gel

Xanthan Gum (Rhodopol) and a biostat (Proxel GXL) are dispersed in water in sufficient amounts to prepare a 2%-gel and vigorously mixed until the Rhodopol is fully wetted. The gel is allowed to sit for 24 hours and mixed again until homogeneous and a viscosity between 650 to 800 mPas in 25% dilution (1 part gel in 3 parts water) (BROOKFIELD viscometer with spindle 3 at 30 rpm and 22° C.) is achieved.

1.3—Active Ingredient Premix

Surfactants (Soprophor 4D384 and Geropon T77) (3.57 parts each) and 0.30 parts silicon oil (Antifoam A) are combined with water and mixed until homogeneous. Six parts Irgalite Red C213, 0.338 parts Fludioxonil tech and 3.226 parts Difenoconazole tech are added and mixed until a homogeneous mixture is achieved. Titanium dioxide (Ti-Pure R-931) (34 parts) is then added and mixed until a homogeneous mixture is achieved.

While maintaining the temperature below 35° C., the mixture is passed through a colloid mill (e.g. attritor or equivalent) and then a wet mill (e.g. a Dyno mill) to achieve a particle size distribution $D_{95}<10.0$ μm (Malvern Master-Sizer S).

1.4—Seed Treatment Formulation

Water and 50 parts of the Active Ingredients Premix (1.3) are charged to a vessel and mixed until uniform. Glycerin (16 parts) followed by 2.5 parts of a polymer 25% sol (Pluronic P103) are added and mixed until homogeneous. Mefenoxam as Apron XL LS (1.524 parts) is added and mixed for at least 15 minutes followed by 8 parts of the 10%-Volclay Gel (1.1) and mix until uniform (at least 15 minutes). Five parts of the 2%-Aqueous Thickener Gel (1.2) is added and and mixed until until substantially homogeneous (evenly dispersed phase) and a target viscosity 400 mPas (BROOKFIELD viscometer with spindle 3 at 30 rpm and 22° C.) is achieved. The formulation is optionally screened through a 100-mesh screen prior to packaging.

Example 2

Preparation of an Inert Seed Treatment Matrix Formulation

An inert seed treatment matrix is prepared by following the procedures given in example 1, but without adding the active ingredients. The matrix formulation can be combined with off-the-shelf seed treatment products in order to enhance performance such as drying time, cold stability and dust-off.

Examples 3–14

Preparation of Enhanced Seed Treatement Compositions

As shown in Table 1, the inert seed treatment matrix of example 2 is combined with the following off-the-shelf seed treatment products in an amount sufficient to achieve an active ingredient concentration of from about 0.5% to about 50% by weight of the final combined composition. The final combined composition is suitable to be applied to seed by spraying, wetting or mixing in a volume of from 200 ml to 3 liters of the final combined position per 100 kg of seed.

TABLE 1

| Example No. | Seed Treatment Product |
|---|---|
| 3 | Allegiance ™-FL |
| 4 | Apron ®-FL fungicide |
| 5 | Baytan 30 flowable fungicide |
| 6 | Captan 30-DD seed protectant |
| 7 | Gaucho ® 600 insecticide |
| 8 | Genesis ™ flowable potato seed-piece treatment insecticide |
| 9 | Kodiak ® flowable biological fungicide |
| 10 | Raxil ®-Thiram flowable fungicide |
| 11 | Thiram 50 WP fungicide |
| 12 | Tops ® MZ potato seed-piece treatment |
| 13 | VITAFLO ®-280 fungicide |
| 14 | Vitavax ®-200 flowable fungicide |

Examples 15–53

Preparation of an Aqueous Seed Treatment Formulation shown in tables 2–4, aqueous compositions of Examples 15–53 are prepared by following the procedures given in example 1. The numbers given in the Examples are concentrations in % weight/weight.

TABLE 2

| | 15 % w/w | 16 % w/w | 17 % w/w | 18 % w/w | 19 % w/w | 20 % w/w | 21 % w/w | 22 % w/w | 23 % w/w | 24 % w/w | 25 % w/w | 26 | 27 |
|---|---|---|---|---|---|---|---|---|---|---|---|---|---|
| Active Ingredients | | | | | | | | | | | | | |
| Fludioxonil tech. | 0.21 | 0.25 | 0.5 | 0.25 | 0.25 | 0.5 | | 0.25 | 0.25 | 0.25 | 0.25 | 0.25 | 0.25 |
| Difenoconazole tech | 2.5 | 3.5 | 7 | 3.5 | 5 | 3.5 | 4 | 3.5 | 3.5 | 3.5 | 3.5 | 3.5 | 3.5 |
| Mefenoxam tech | 1.5 | 1 | 2 | 1 | 1.5 | 1 | 2 | 1 | 2 | 1 | 1 | 1 | 1 |
| Azoxystrobin tech | | | | 1 | | | 2 | | | | | | |
| Antifreeze | | | | | | | | | | | | | |
| Glycerine | 18 | 8 | 12 | 16 | 19 | 9 | | | | 1.5 | 15 | 15 | 15 |
| Ethylenglycol | | | | | | | 15 | 9 | | | | | |
| Propylenglycol | | | | | | 9 | | | 15 | | | | |
| Surface active agents | | | | | | | | | | | | | |
| Geropon T77 | 2 | | 2 | | | 2 | | | | | | | |
| Soprophor 4D384 | 2.1 | 4 | 2 | 2 | | | | | | 1.5 | 1.5 | 0.5 | 1.5 |

TABLE 2-continued

|  | 15 % w/w | 16 % w/w | 17 % w/w | 18 % w/w | 19 % w/w | 20 % w/w | 21 % w/w | 22 % w/w | 23 % w/w | 24 % w/w | 25 % w/w | 26 | 27 |
|---|---|---|---|---|---|---|---|---|---|---|---|---|---|
| Stepan Agent 1411-80A | 0.2 | 0.2 |  | 0.2 |  |  |  | 0.2 | 0.2 | 0.2 | 0.2 | 0.2 | 0.2 |
| Reax 825 |  |  | 1 | 4 | 1 | 2 |  |  |  | 1.5 | 1.5 | 0.2 | 1.5 |
| Genapol X-060 |  |  |  |  | 4 |  |  |  |  |  |  |  |  |
| Polymeric Materials |  |  |  |  |  |  |  |  |  |  |  |  |  |
| Agrimer ST |  |  |  | 2 |  |  |  |  |  |  |  |  |  |
| Pluronic P103 | 2.6 |  | 2.6 | 2 |  |  |  |  |  |  |  |  |  |
| Pluronic P65 |  |  |  |  | 4 |  |  |  |  |  |  |  |  |
| Pluronic P108 |  |  |  |  |  | 3 |  |  |  |  |  |  |  |
| Vinamul 18160 |  |  |  |  |  |  | 2 |  |  | 3 | 3 | 3 | 0.25 |
| Agrimer 30 |  |  |  |  |  |  |  | 2 |  |  |  |  |  |
| Agrimer VA 7w |  | 2 |  |  |  |  |  |  |  |  |  |  |  |
| Agrimer AL 10 |  |  |  |  |  |  |  |  | 1 |  |  |  |  |
| PEG 400 |  |  |  |  |  |  |  |  | 1 |  |  |  |  |
| Witconol NS 500LQ |  |  |  |  |  |  |  |  |  |  |  |  |  |
| Carriers |  |  |  |  |  |  |  |  |  |  |  |  |  |
| TiO2 | 17 | 17 | 10 |  |  | 15 |  |  |  | 14 | 2 | 14 | 14 |
| Volcaly 325mesh | 1 | 0.5 |  | 0.5 |  | 0.5 |  | 2 | 3 |  |  |  |  |
| Talc |  |  | 5 | 15 | 12 | 2 | 10 | 3 | 2 |  |  |  |  |
| Others |  |  |  |  |  |  |  |  |  |  |  |  |  |
| Irgalite Red C2B |  |  | 5 | 5 | 5 | 5 | 5 | 4 |  |  |  |  |  |
| Antifoam A | 0.12 | 0.12 | 0.12 | 0.12 | 0.12 | 0.12 | 0.12 | 0.12 | 0.12 | 0.12 | 0.12 | 0.12 | 0.12 |
| Proxel GXL | 0.1 | 0.1 | 0.1 | 0.1 | 0.1 | 0.1 | 0.1 | 0.1 | 0.1 | 0.1 | 0.1 | 0.1 | 0.1 |
| Rhodopol 23 | 0.25 | 0.25 | 0.25 | 0.25 | 0.25 | 0.25 | 0.25 | 0.25 | 0.25 | 0.25 | 0.25 | 0.25 | 0.25 |
| water | Add 100 | add 100 | add 100 | add 100 | add 100 | add 100 | add 100 | add 100 | add 100 | add 100 | add 100 | add 100 | add 100 |

TABLE 3

|  | 28 % w/w | 29 % w/w | 30 % w/w | 31 % w/w | 32 % w/w | 33 % w/w | 34 % w/w | 35 % w/w | 36 % w/w | 37 | 38 | 39 | 40 |
|---|---|---|---|---|---|---|---|---|---|---|---|---|---|
| Active Ingredients |  |  |  |  |  |  |  |  |  |  |  |  |  |
| Fludioxonil tech. | 3.5 | 2 | 3.5 | 7 | 5 | 2 | 0.5 | 1 | 3.5 |  |  |  |  |
| Difenoconazole tech |  |  |  |  |  | 5 |  |  |  | 3.5 | 3.5 | 3.5 | 3.5 |
| Mefenoxam tech | 1.1 | 0.7 | 1.1 | 2 | 1 | 1.1 | 1.1 | 1.1 | 1.1 | 1.1 | 1.1 | 1.1 | 1.1 |
| Myclobutanil tech | 9 | 6 | 9 | 18 | 15 | 9 | 9 | 9 | 9 | 9 | 9 | 9 | 9 |
| Antifreeze |  |  |  |  |  |  |  |  |  |  |  |  |  |
| Glycerine |  |  |  | 2 | 10 | 14 |  | 5 |  | 2 | 14 | 14 | 14 |
| Ethylenglycol | 7.1 | 7.1 | 7.1 | 7.1 |  |  |  | 5 | 15 |  |  |  |  |
| Propylenglycol |  |  |  |  |  |  | 14 | 5 |  |  |  |  |  |
| Surface active agents |  |  |  |  |  |  |  |  |  |  |  |  |  |
| Geropon T77 | 1 | 1 | 1 | 2 |  | 4 | 3 |  |  | 1 | 1 | 0.5 | 1 |
| Soprophor 4D384 | 1 | 1 | 1 |  | 2 |  | 1 | 3 |  | 1 | 1 | 0.5 | 1 |
| Stepan Agent 1411-80A | 0.2 | 0.2 | 0.2 |  |  |  |  |  |  | 0.2 | 0.2 | 0.2 | 0.2 |
| Reax 825 |  |  |  |  | 2 |  |  | 0.5 | 2 |  |  |  |  |
| Genapol X-060 |  |  |  | 2 |  |  |  | 0.5 | 2 |  |  |  |  |
| Polymeric Materials |  |  |  |  |  |  |  |  |  |  |  |  |  |
| Agrimer ST |  | 2 |  |  |  |  |  |  |  |  |  |  |  |
| Pluronic P103 | 1.5 |  | 3 |  |  |  |  |  |  | 2 | 2 | 2 | 0.3 |
| Pluronic P65 |  |  |  | 2 |  |  |  |  |  |  |  |  |  |
| Pluronic P108 |  |  |  |  | 2 |  |  |  |  |  |  |  |  |
| Vinamul 18160 |  |  |  |  |  | 1.5 |  |  |  |  |  |  |  |
| Agrimer 30 |  |  |  |  |  |  | 2 |  |  |  |  |  |  |
| Agrimer VA 7w |  |  |  |  |  |  |  | 3 |  |  |  |  |  |
| Agrimer AL 10 |  |  |  |  |  |  |  |  | 2 |  |  |  |  |
| PEG 400 | 1 | 1 | 1 | 1 | 1 | 1 | 1 | 1 | 1 |  |  |  |  |
| Witconol NS 500LQ |  |  |  |  |  |  |  |  |  |  |  |  |  |
| Carriers |  |  |  |  |  |  |  |  |  |  |  |  |  |
| TiO2 | 5 |  |  |  | 1 | 10 | 15 |  |  |  |  |  |  |
| Volcaly 325mesh | 1 |  |  |  | 1 |  |  |  |  |  |  |  |  |
| Talc |  | 5 | 6 | 7 | 8 | 3 | 3 |  | 15 | 5 | 1 | 5 | 5 |

TABLE 3-continued

| | 28 % w/w | 29 % w/w | 30 % w/w | 31 % w/w | 32 % w/w | 33 % w/w | 34 % w/w | 35 % w/w | 36 % w/w | 37 | 38 | 39 | 40 |
|---|---|---|---|---|---|---|---|---|---|---|---|---|---|
| Others | | | | | | | | | | | | | |
| Irgalite Red C2B | | | | | | | | | | | | | |
| Antifoam A | 0.12 | 0.12 | 0.12 | 0.12 | 0.12 | 0.12 | 0.12 | 0.12 | 0.12 | 0.12 | 0.12 | 0.12 | 0.12 |
| Proxel GXL | 0.1 | 0.1 | 0.1 | 0.1 | 0.1 | 0.1 | 0.1 | 0.1 | 0.1 | 0.1 | 0.1 | 0.1 | 0.1 |
| Rhodopol 23 | 0.25 | 0.25 | 0.25 | 0.25 | 0.25 | 0.25 | 0.25 | 0.25 | 0.25 | 0.25 | 0.25 | 0.25 | 0.25 |
| Water | add 100 | add 100 | add 100 | add 100 | add 100 | add 100 | add 100 | add 100 | add 100 | add 100 | add 100 | add 100 | add 100 |

TABLE 4

| | 41 % w/w | 42 % w/w | 43 % w/w | 44 % w/w | 45 % w/w | 46 % w/w | 47 % w/w | 48 % w/w | 49 % w/w | 50 % w/w | 51 % w/w | 52 % w/w | 53 % w/w |
|---|---|---|---|---|---|---|---|---|---|---|---|---|---|
| Active Ingredients | | | | | | | | | | | | | |
| Carboxim tech. | 10 | | | 15 | 1 | | | | 1 | | | | |
| Tebuconazol tech. | | 1 | 3 | 1 | 3 | | 3 | | | 3 | 3 | 3 | 3 |
| Metalaxyl M tech. | | | 1 | 1.5 | 1 | | 2 | 1 | 1 | 1 | 1 | 1 | 1 |
| Thiram tech | 10 | 10 | 10 | | 5 | 10 | 10 | | | 10 | 10 | 10 | 10 |
| Captan tech | | | | | 10 | | | | | | | | |
| Ipotrione tech | | | | | 15 | 10 | | 12 | 15 | 10 | 10 | 10 | 10 |
| Triticonazole tech | | | | | | | | 2 | 3 | | | | |
| Antifreeze | | | | | | | | | | | | | |
| Glycerine | 18 | 14 | 18 | | | 18 | | 10 | 2 | | | | |
| Ethylenglycol | | | | | | | 15 | | 2 | 2 | 14 | 14 | 14 |
| Propylenglycol | | | | 15 | 10 | | | 3 | 10 | | | | |
| Surface active agents | | | | | | | | | | | | | |
| Geropon T77 | 2 | | | 1.5 | | 1 | | 2.5 | 1 | | | | |
| Soprophor 4D384 | 2.1 | 3 | | | | | 1.5 | | 2 | 2 | 2 | 0.15 | 2 |
| Stepan Agent 1411-80A | 0.2 | 0.2 | | | 3 | | | | | | | | |
| Reax 825 | | 1 | 2 | 2.5 | 1 | | 2.5 | 2.5 | | 2 | 2 | 0.15 | 2 |
| Genapol X-060 | | | 3 | | | 3 | | | 1 | | | | |
| Polymeric Materials | | | | | | | | | | | | | |
| Agrimer ST | 2 | 3 | | | | | | | | | | | |
| Pluronic P103 | | | 2 | | | | | | | | | | |
| Pluronic P65 | | | | 1 | | | | | | 3 | 3 | 3 | 0.4 |
| Pluronic P108 | | | | | 1.5 | | | | | | | | |
| Vinamul 18160 | | | | | | 2.5 | | | | | | | |
| Agrimer 30 | | | | | | | 2 | | | | | | |
| Agrimer VA 7w | | | | | | | | | 2 | | | | |
| Agrimer AL 10 | | | | 1 | | | | | 2 | | | | |
| PEG 400 | | | | 0.5 | 1 | | | | 1 | | | | |
| Witconol NS 500LQ | | | | | | | 1 | 1 | | | | | |
| Carriers | | | | | | | | | | | | | |
| TiO2 | 5 | 10 | 15 | | | 15 | 18 | 10 | | 5 | 1 | 5 | 5 |
| Volcaly 325mesh | 1 | | | 3 | 2 | 0.5 | | | 0.5 | | | | |
| Talc | 5 | | | 2 | 10 | | | 2 | 15 | 5 | 1 | 5 | 5 |
| Others | | | | | | | | | | | | | |
| Irgalite Red C2B | | 5 | 5 | 5 | 5 | 5 | 4 | | | | | | |
| Antifoam A | 0.12 | 0.12 | 0.12 | 0.12 | 0.12 | 0.12 | 0.12 | 0.12 | 0.12 | 0.12 | 0.12 | 0.12 | 0.12 |
| Proxel GXL | 0.1 | 0.1 | 0.1 | 0.1 | 0.1 | 0.1 | 0.1 | 0.1 | 0.1 | 0.1 | 0.1 | 0.1 | 0.1 |
| Rhodopol 23 | 0.25 | 0.25 | 0.25 | 0.25 | 0.25 | 0.25 | 0.25 | 0.25 | 0.25 | 0.25 | 0.25 | 0.25 | 0.25 |
| water | add 100 | add 100 | add 100 | add 100 | Add 100 | add 100 | add 100 | add 100 | add 100 | add 100 | add 100 | add 100 | add 100 |

Example 54 and Comparative Examples A–D

Aqueous compositions of Examples 54 and A–D are prepared by following the procedures given in example 1. The numbers given in the Examples are concentrations in % weight/weight.

TABLE 5

| Ingredients | 54 | A | B | C | D |
|---|---|---|---|---|---|
| Difenoconazole tech | 1.67 | 1.67 | 1.67 | 1.67 | 1.67 |
| Fludioxonil tech | 0.17 | 0.17 | 0.17 | 0.17 | 0.17 |
| Mefenoxam | 0.5 | 0.5 | 0.5 | 0.5 | 0.5 |
| Stepan Agent 1411-80A | 0.2 | 0.2 | 0.2 | 0.2 | 0.2 |
| TiO2 | 20.0 | 2.0 | 20.0 | 20.0 | 20.0 |
| Irgalite Red C2B | 4.0 | 4.0 | 4.0 | 4.0 | 4.0 |
| Soprophor 4D384 | 2.0 | 2.0 | 2.0 | 0.2 | 2.0 |
| Reax 825 | 2.0 | 2.0 | 2.0 | 0.2 | 2.0 |
| Antifoam A | 0.1 | 0.1 | 0.1 | 0.1 | 0.1 |
| Glycerine | 18 | 18 | 2.5 | 18 | 18 |
| Pluronic P103 | 2.0 | 2.0 | 2.0 | 2.0 | 0 |
| Xantham gum | 0.1 | 0.1 | 0.1 | 0.1 | 0.1 |
| Proxel GXL | 0.1 | 0.1 | 0.1 | 0.1 | 0.1 |
| Water | Add 100 | add 100 | add 100 | add 100 | add 100 |

The physical properties of seed treated with the composition of Example 54 are compared with the properties of seed treated with the compositions of examples A–D.

1. Accelerated Storage Stability Testing (1 months at 50C)—this simulates roughly 2 years at ambient temperature. Accepatble range is 100–1000 mPas.

|  | 54 | A | B | C | D |
|---|---|---|---|---|---|
| % phase separation | 2% | 4% | 3% | 35% | 2% |
| Viscosity (mPas) | 350 | 285 | 315 | 3500 | 410 |

Commercial product: Dividend XL RTA: 2% phase sep., viscosity 210 mPas.
Raxil FL: 18% phase sep., viscosity 100 mPas.

2. Drying time (Seeds (wheat) are treated (at label rate) at RT in a Hege® Seed Treater, and we record the time it takes for them to dry). Acceptable range is below 1 minute

|  | 54 | A | B | C | D |
|---|---|---|---|---|---|
| Drying time (seconds): | 35 | 180 | 30 | 40 | 30 |

Commercial product: Dividend XL RTA: 40 seconds
Raxil FL: 50 seconds

3. Cold stability (frozen seed (at −18 C) are treated (at label rate) at RT in a Hege® Seed Treater, and we record the seed coverage homogeneity). Homogeneity must be good to pass the test

|  | 54 | A | B | C | D |
|---|---|---|---|---|---|
| Coverage homogeneity | Good | Medium | poor* | Good | good |

*'spots' of product on part of the seed, part of the seed is not covered at all, the seeds tend to stick together, some seed are 'overtreated' while some other are not treated at all
Commercial product: Dividend XL RTA: good
Raxil FL: good 4. Dust-off (treated seed (wheat), once dry, are tumbled in a close system under vacuum (standard dust-off equipment, known by all seed companies). There is an air flow which is maintained through the container, and which is filtered through a 5 micron sieve. After 5 minutes the amount of dust on the filter is recorded. Acceptable range is below 2.5 mg

|  | 54 | A | B | C | D |
|---|---|---|---|---|---|
| Dust-off (mg) | 2.0 | 0.7 | 1.3 | 2.1 | 5.6 |

Commercial product: Dividend XL RTA: 1.8 mg
Raxil FL: 5.0 mg

It is apparent from the above data that seeds treated with the inventive composition of Example 54 are much better than the seeds treated with the comparative compositions. For comparative purposes, the seeds were coated with each of the film-forming polymers which together comprise the coating of Example 1. The data shows that each of these materials taken separately result in poor performance regarding storage stability, drying time, cold stability and dustiness. The above data highlights the surprising efficacy of the composition of Example 54.

Although the foregoing invention has been described in some detail by way of illustration and example for purposes of clarity of understanding, it will be apparent that various changes and modifications may be practiced within the scope of the appended claims.

What is claimed is:

1. An aqueous composition suitable for applying fungicides to plant propagation materials comprising a fungicidally effective amount of at least one fungicidally active compound selected from the group consisting of difenoconazole, Metalaxyl-M, fludioxonil, and azoxystrobin, water and a blend of the following components, by weight:
   a) 2–10% of at least one surface-active agent, comprising
      a1) at least one anionic surfactant;
   b) 0.5–10% of at least one polymer selected from water-dispersible and water-soluble film-forming polymers;
   c) 4–20% of at least one inorganic solid carrier; and
   d) 3–20% of at least one antifreeze agent.

2. The composition according to claim 1, wherein component a) is at least one of sodium N-methyl-N-oleoyl taurate, polyarylphenol polyalkoxyether phosphate, and a salt form of ethoxylated tristyrylphenol sulfate.

3. The composition according to claim 1, wherein component b) is at least one of propyleneoxide-ethyleneoxide-copolymer and butanol PO-EO copolymer.

4. The composition according to claim 1, wherein component c) is at least one of magnesium silicate and titanium dioxide.

5. The composition according to claim 1, wherein component d) is at least one of ethylene glycol, propylene glycol, and glycerine.

6. The composition according to claim 1, wherein component a) is at least one of sodium N-methyl-N-oleoyl taurate, polyarylphenol polyalkoxyether phosphate, and a salt form of ethoxylated tristyrylphenol sulfate; component b) is at least one of propyleneoxide-ethyleneoxide-copolymer and butanol PO-EO copolymer; component c) is at least one of magnesium silicate and titanium dioxide; and component d) is at least one of ethylene glycol, propylene glycol, and glycerine.

7. The composition according to claim 6, further comprising one or more of a wetting agent, a pigment, an antifoam agent, a thickener, and a preservative.

8. The composition according to claim 7, wherein the at least one fungicidally active compound is difenconazole and Metalaxyl-M, component a) is ethoxylated tristyrlphenol sulfate ammonium salt and sodium N-methyl-N-oleoyl taurate, component b) is propyleneoxide-ethyleneoxide copolymer, component c) is magnesium silicate, and component d) is ethylene glycol and glycerine.

9. The composition according to claim 7, further comprising myclobutanil.

10. The composition according to claim 9, wherein a) is ethoxylated tristyrlphenol sulfate ammonium salt and sodium N-methyl-N-oleoyl taurate, component b) is propyleneoxide-ethyleneoxide copolymer, component c) is magnesium silicate, and component d) is ethylene glycol and glycerine.

11. An aqueous composition suitable for applying fungicides to plant propagation materials comprising a fungicidally effective amount of at least one fungicidally active compound selected from the group consisting of Benomyl (also known as Benlate), Bitertanol, Captan, Carbendazim, Carboxin (also known as Carbathiin), Capropamid, Chlorothalonil, Cymoxanil, Cyprodinil, Difenoconazole, Ethirimol, Fenpiclonil, Fenpropimorph, Fludioxonil, Fluquinconazole, Flutolanil, Flutriafol, Fosetyl-aluminum, Fuberidazole, Guazatine, Hymexanol, Kasugamycin, Imazalil, Imibenconazole, Iminoctadine-triacetate, Ipconazole, Iprodione, Mancozeb, Maneb, Mepronil, Metalaxyl, Metalaxyl-M (Mefenoxam), Metconazole, Metiram, MON 65500 (Silthiopham-ISO proposed), Myclobutanil, Nuarimol, Oxadixyl, Oxine-copper, Oxolinic acid, Pefurazoate, Pencycuron, Prochloraz, Propamocarb hydrochloride, Pyroquilon, Quintozene (also known as PCNB), Tebuconazole, Tecnazene, Tetraconazole, Thiabendazole, Thifluzamide, Thiophenate-methyl, Thiram, Tolclofos-methyl, Triadimenol, Triazoxide, Triflumizole, trifloxystrobin, azoxystrobin, kresoxim-methyl, picoxystrobin and Triticonazole; water, and a blend of the following components, by weight:

a) 2–10% of at least one surface-active agent, comprising
a1) at least one anionic surfactant;
b) 0.5–10% of at least one polymer selected from water-dispersible and water-soluble film-forming polymers;
c) 4–20% of at least one inorganic solid carrier; and
d) 3–20% of at least one antifreeze agent.

12. The composition according to claim 11, wherein the at least one fungicidally active compound is selected from carboxin, cyprodinil, chlorothalonil, difenoconazole, fludioxonil, metalaxyl, metalaxyl-M, myclobutanil, tebuconazole, thiabendazole, thiram, trifloxystrobin, azoxystrobin, picoxystrobin, and triticonazole, component a) is at least one of sodium N-methyl-N-oleoyl taurate, polyarylphenol polyalkoxyether phosphate, and a salt form of ethoxylated tristyrylphenol sulfate; component b) is at least one of propyleneoxide-ethyleneoxide -copolymer and butanol PO-EO copolymer; component c) is at least one of magnesium silicate and titanium dioxide; and component d) is at least one of ethylene glycol, propylene glycol, and glycerine.

* * * * *